(12) United States Patent
Akatsuka et al.

(10) Patent No.: US 7,631,539 B2
(45) Date of Patent: Dec. 15, 2009

(54) GAS SENSOR PRODUCTION METHOD AND GAS SENSOR

(75) Inventors: Shoji Akatsuka, Aichi (JP); Kouji Ogawa, Aichi (JP); Kiyoharu Imaeda, Aichi (JP); Nobuo Kawai, Gifu (JP); Osamu Shinkai, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 298 days.

(21) Appl. No.: 10/585,450

(22) PCT Filed: Jan. 5, 2005

(86) PCT No.: PCT/JP2005/000031

§ 371 (c)(1),
(2), (4) Date: Jul. 7, 2006

(87) PCT Pub. No.: WO2005/066617

PCT Pub. Date: Jul. 21, 2005

(65) Prior Publication Data

US 2007/0167079 A1    Jul. 19, 2007

(30) Foreign Application Priority Data

Jan. 9, 2004    (JP)    ............................. 2004-004861

(51) Int. Cl.
*G01N 9/00*    (2006.01)
(52) U.S. Cl. .................................................. 73/31.05
(58) Field of Classification Search ................ 73/23.2,
73/31.05, 23.31, 23.32, 23.33
See application file for complete search history.

(56) References Cited

U.S. PATENT DOCUMENTS

| | | | | |
|---|---|---|---|---|
| 5,859,361 A * | 1/1999 | Fukaya et al. | ................. | 73/23.2 |
| 6,178,806 B1 * | 1/2001 | Watanabe et al. | .......... | 73/23.32 |
| 6,258,234 B1 * | 7/2001 | Watanabe et al. | ........... | 204/424 |
| 6,945,091 B2 * | 9/2005 | Nakagawa | .................. | 73/31.05 |
| 2002/0100312 A1 * | 8/2002 | Jackson et al. | ............. | 73/31.05 |
| 2003/0150254 A1 * | 8/2003 | Fujita et al. | ................... | 73/23.2 |
| 2004/0040370 A1 * | 3/2004 | Kojima | ....................... | 73/31.05 |
| 2005/0138989 A1 * | 6/2005 | Noda et al. | ................. | 73/31.05 |
| 2008/0121020 A1 * | 5/2008 | Oya et al. | ................... | 73/31.05 |

FOREIGN PATENT DOCUMENTS

| | | |
|---|---|---|
| DE | 197 03 458 A1 | 7/1997 |
| JP | 4-2959 A | 1/1992 |
| JP | 8-15214 A | 1/1996 |
| JP | 9-54063 A | 2/1997 |
| JP | 9-229897 A | 9/1997 |
| JP | 10-332627 A | 12/1998 |
| JP | 11-271254 A | 10/1999 |
| JP | 2000-81412 A | 3/2000 |
| JP | 2003-194764 | 7/2003 |
| JP | 2003-194764 A | 7/2003 |

* cited by examiner

*Primary Examiner*—Hezron Williams
*Assistant Examiner*—Gunnar J Gissel
(74) *Attorney, Agent, or Firm*—Sughrue Mion, PLLC

(57) ABSTRACT

A method of producing a gas sensor is provided. The method includes a disposition step of preparing an elastic seal member having a main body portion and a smaller diameter portion that is smaller in outer diameter than the main body portion, disposing the entire main body portion and a part of the smaller diameter portion inside a tubular metallic member and allowing a remaining part of the smaller diameter portion to protrude outward from a rear end of the tubular metallic member, and a crimping step of crimping at least a portion of the tubular metallic member radially inward and thereby compressively deforming the elastic seal member. A gas sensor is also provided.

9 Claims, 8 Drawing Sheets

FIG.3
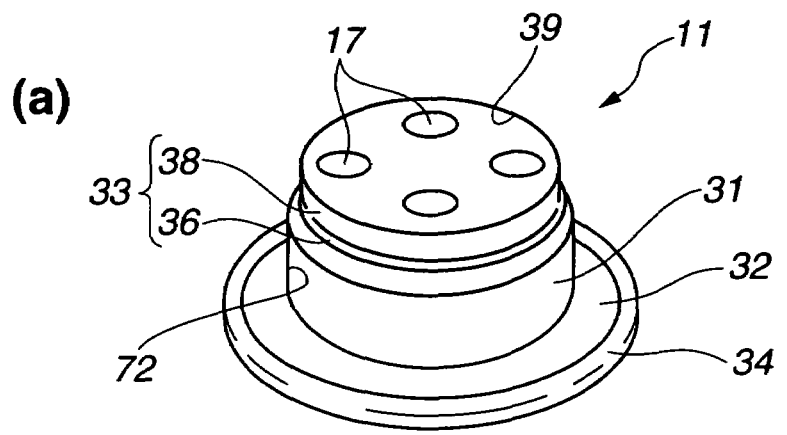
(a)
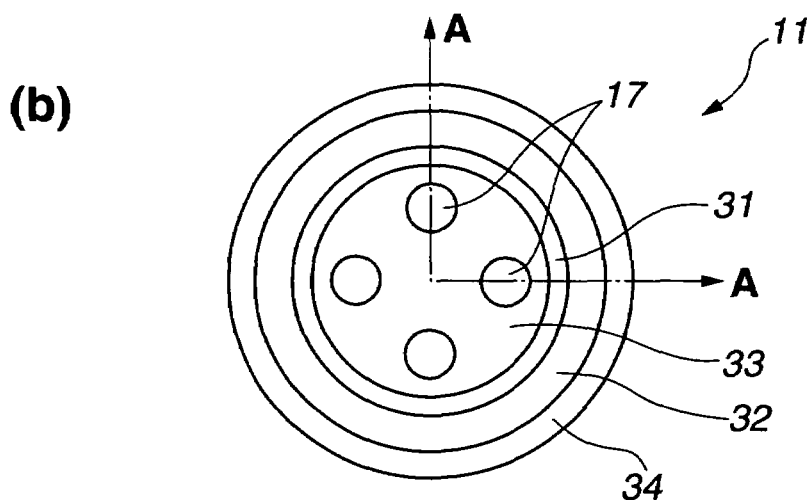
(b)
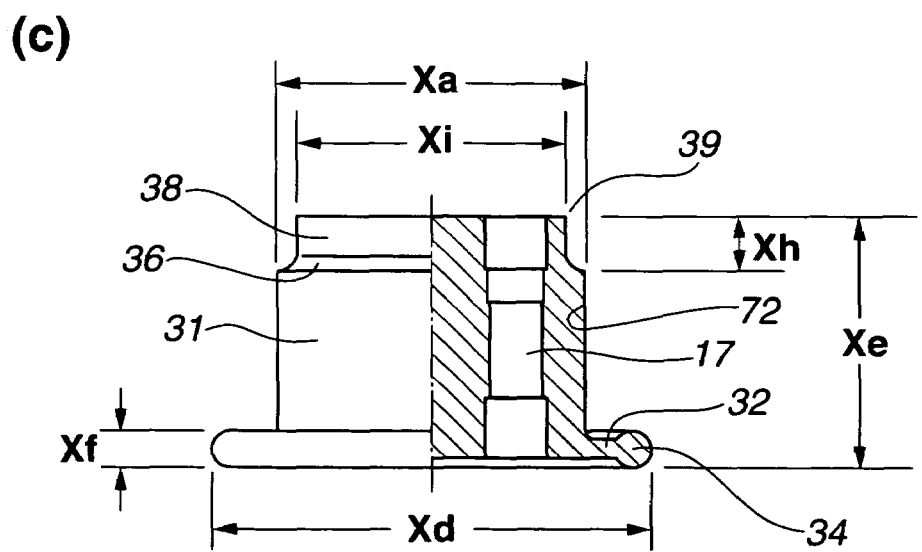
(c)

GAS SENSOR PRODUCTION METHOD AND GAS SENSOR

This is a national stage entry of PCT/JP05/00031, filed on Jan. 5, 2005. This also claims a foreign priority to JP Ser. No. 2004-004861, filed Jan. 9, 2004.

TECHNICAL FIELD

The present invention relates to a gas sensor production method and a gas sensor. More specifically, the present invention relates to a method of producing a gas sensor for detecting a concentration of a particular gas component in an exhaust gas emitted from an internal combustion engine, such as an Oxygen sensor, NOx sensor and HC sensor, and a gas sensor.

BACKGROUND TECHNIQUE

A gas sensor having a sensor element that varies in electric characteristics in response to a concentration of a particular gas component in an exhaust gas has heretofore been used for an air/fuel ratio control of an automotive vehicle. As such a gas sensor is known, for example, such one that is configured to include a cup-shaped sensor element formed of an oxygen ion conductive solid electrolyte, a heater for heating the sensor element, a metallic housing for holding the sensor element, a tubular metallic member provided to a rear end side of the metallic housing, and lead wires electrically connected to the sensor element and the heater and pulled out from an inside of the tubular metallic member to the outside thereof. The lead wires used for the gas sensor are generally formed by covering conductor wires electrically connected to a sensor element and heater by an insulating film.

In such a gas sensor, it is known a technique for fixing, after a cylindrical elastic seal member having lead wire insertion holes for insertion of the above-described lead wires is disposed inside the tubular metallic member, the elastic seal member is fixed to a tubular metallic member by crimping the tubular metallic member radially inward (refer to Patent Document 1 and Patent Document 2). By employing this technique, the air-tightness between the elastic seal member and the tubular metallic member and between the lead wire and the elastic seal member can be higher, and waterproof of the inside of the tubular metallic member can be attained.

Patent Document 1: Unexamined Japanese Patent Publication No. 9-229897

Patent Document 2: Unexamined Japanese Patent Publication No. 9-54063

In the meantime, an attempt for saving space around an exhaust pipe of in an automotive vehicle is being made in recent years so that there may occur such a case in which a freedom concerning a position for installation of a gas sensor on an exhaust pipe is restricted. Due to this, there arises such a case in which at the time the lead wires pulled out of the tubular metallic member after the sensor is installed on the exhaust pipe are connected to an external circuit such as ECU, they need to be bent leftward and rightward at the points adjacent the rear end opening edge portions of the lead wire insertion holes. Further, there is such a case in which the lead wires pulled toward the rear end side of the gas sensor need to be bent by nearly 180 degrees toward the front end side (element side) and connected to the external circuit.

However, at the time the lead wires of the gas sensor configured so that the rear end peripheral edge of the elastic seal member is positioned at the more front end side than the rear end of the tubular metallic member is connected to an external circuit, there may be caused such a problem that the lead wires are damaged when bent leftward and rightward at the points adjacent the rear end opening edge portions of the lead wire insertion holes. Namely, when the lead wires are bent leftward and rightward at the points adjacent the rear end opening edge portions of the lead wire insertion holes, they are brought into contact with an edge or burr existing at the rear end portion of the tubular metallic member such that there is caused a possibility that when a worker for an wiring operation pulls the lead wires under such a condition, the insulating film is rubbed by the edge or burr to be broken or in the worst case the conductor wire is broken. This problem is liable to be caused particularly when the lead wires are bent by nearly 180 degrees as described above.

Thus, it is considered such a countermeasure that the height of the elastic seal member is increased so as to allow the rear end side thereof to protrude from the rear end of the tubular metallic member so that the lead wires do not directly contact the edge or burr of the tubular metallic member even when the lead wires are bent leftward and rightward, for thereby preventing damage of the lead wires.

However, by the investigation conducted by the inventors it was revealed that a countermeasure of making the rear end side of the cylindrical elastic seal member simply protrude from the rear end of the tubular metallic member caused a new problem that when thermal expansion of the elastic seal member occurred during use of the gas sensor at elevated temperature, stress was locally caused at the elastic seal member due to rubbing with the edge or burr of the tubular metallic member, thus causing a crack in the elastic seal member. In the meantime, when a crack is caused in the elastic seal member, the gas sensor cannot maintain the airtightness and waterproof.

SUMMARY OF THE INVENTION

The present invention has been made in view of the above-described problem and has for its object to provide a gas sensor that is capable of preventing the lead wires from being damaged when being bent while being capable of preventing the lead wires from being cracked even when the elastic seal member is thermally expanded during use of the gas sensor. Further, it is an object of the present invention to provide a method of producing a gas sensor having such a high reliability.

According to an aspect of the present invention there is provided a method of producing a gas sensor having a sensor element extending in an axial direction and having a front end side to face a measured gas, a metallic housing radially surrounding the sensor element and holding the sensor element, a tubular metallic member provided to a rear end side of the metallic housing, at least one lead wire extending from an inside to an outside of the tubular metallic member and having a conductor wire electrically connected to the sensor element and an insulating film covering the conductor wire, and an elastic seal member having a lead wire insertion hole into which the lead wire is inserted, characterized by comprising:

a disposition step of preparing the elastic seal member having a main body portion and a smaller diameter portion smaller in outer diameter than the main body portion, disposing the entire main body portion and a part of the smaller diameter portion inside the tubular metallic member and allowing the a remaining part of the smaller diameter portion to protrude outward from a rear end of the tubular metallic member; and a crimping step of crimping at least a portion of the tubular metallic member radially inward and compressively deforming the elastic seal member.

In the method of producing a gas sensor according to the present invention, the elastic seal member having the main body portion and the smaller diameter portion smaller in outer diameter than the main body portion is prepared beforehand. Thereafter, the disposition step of disposing the elastic seal member inside the tubular metallic member and the crimping step of crimping a portion of the tubular metallic member radially inward and fixing the elastic seal member to the tubular metallic member are performed in sequence.

Herein, in the disposition step, the elastic seal member is disposed inside the tubular metallic member by moving at least one of the elastic seal member and the tubular metallic member in the direction to allow them to go closer to each other. In this instance, in the disposition step in the method of producing a gas sensor according to the present invention, the entire main body portion and a part of the smaller diameter portion are disposed inside the tubular metallic member and a remaining part of the smaller diameter portion is protruded outward from the rear end of the tubular metallic member.

By performing the crimping step after such a disposition step, the outer circumferential surface of not the main body portion but the smaller diameter portion of the elastic seal member can be disposed astride the rear end of the tubular metallic member when observed with respect to the axial direction of the gas sensor.

By this, the gas sensor obtained by the method of the present invention is configured so that a part of the smaller diameter portion of the elastic seal member protrudes from the rear end of the tubular metallic member and the lead wire is hard to directly contact an edge or burr of the tubular metallic member even if bent rightward or leftward at the time of connection to an external device, thus making it possible to prevent damage of the lead wire.

Further, the gas sensor obtained by the present invention, since the outer circumferential surface of the smaller diameter portion is disposed astride the rear end of the tubular metallic member and even when the elastic seal member is thermally expanded during use of the gas sensor, can make smaller the stress caused by an edge or burr existing at the rear end portion of the tubular metallic member as compared with a gas sensor configured so that a portion of a cylindrical elastic seal member simply protrudes from a rear end of a tubular metallic member. Namely, the method of the present invention makes it possible to attain a gas sensor that is hard to cause a crack in an elastic seal member though a portion of the elastic seal member is protruded from the rear end of the tubular metallic member.

Herein, while the gas sensor obtained by the present invention can prevent occurrence of a crack at the time of thermal expansion of the elastic seal member as described above so long as the outer circumferential surface of the smaller diameter portion is disposed astride the rear end of the tubular metallic member, it is preferable for the purpose of preventing occurrence of a crack more effectively that a space remains between the outer circumferential surface of the smaller diameter portion and the rear end of the tubular metallic member after the crimping step. However, in the present invention, the outer circumferential surface of the smaller diameter portion may contact the rear end of the tubular metallic member after the crimping step. This is because even if the outer circumferential surface of the smaller diameter portion contacts the rear end of the tubular metallic member, a resulting contact pressure is smaller as compared with a case where the outer circumferential surface of the main body portion contact the rear end of the tubular metallic member, and therefore an effect of making a crack be hard to be caused at the time of thermal expansion of the elastic seal member can be expected.

Thus, by the method of producing a gas sensor according to the present invention, it becomes possible to produce a gas sensor that is highly reliable and capable of preventing damage of a lead wire caused by bending of the lead wire and a crack in the elastic seal member caused at the time of thermal expansion of the elastic seal member during use of the gas sensor.

In the meantime, in the gas sensor, a single lead wire or a plurality of rear wires may be electrically connected to the sensor element. A single lead wire is used in such a case where one sensor signal is outputted by the lead wire and another sensor signal is a grounding potential and outputted through the metallic housing and the tubular metallic member. Further, a plurality of lead wires are used in such a case where a positive signal and a negative signal are outputted.

Further, a lead wire extending through the lead wire insertion hole of the elastic seal member from the inside to the outside of the tubular metallic member essentially includes a lead wire electrically connected to the above-described sensor element and in addition may include a lead wire for a heater, which is electrically connected to a ceramic heater separately provided for heating the sensor element.

In the meantime, in order that the outer circumferential surface of the smaller diameter portion of the elastic seal member is disposed astride the rear end of the tubular metallic member when observed with respect to the axial direction of the gas sensor, the above-described disposition step is a most noticeable step but it is preferable in the crimping step to perform crimping of the tubular metallic member so that the outer circumferential surface of the main body portion of the elastic seal member does not protrude outward from the rear end of the tubular metallic member after crimping. In the meantime, in order to perform crimping of the tubular metallic member so that the outer circumferential surface of the main body portion of the elastic seal member does not protrude outward from the rear end of the tubular metallic member after crimping, it will suffice to adjust the rate of deformation of the tubular metallic member by crimping suitably in consideration of the material, hardness, etc. of the tubular metallic member and the elastic seal member. Further, the method of crimping for the crimping step is not limited particularly, and multi-angular round crimping such as six-directional round crimping (round crimping using a crimping tool separated into six sections which are moved in six radial directions) and eight-directional round crimping may be enumerated.

Further, in the above-described method of producing a gas sensor, it is preferably that the elastic seal member protrudes outward from the rear end of the tubular metallic member along the axial direction by 0.6 mm or more after the crimping step.

By producing the gas sensor in which the length by which the elastic seal member protrudes outward from the rear end of the tubular metallic member is 6 mm or more, the elastic seal member is liable to be disposed between the lead wire and an edge or burr of the tubular metallic member even when the lead wire is bent nearly 180 degrees at a point adjacent the rear end opening edge portion of the lead wire insertion hole of the elastic seal member that serve, thus making it possible to obtain the gas sensor that is capable of preventing damage of the lead wire more effectively.

In the meantime, in order that the length by which the elastic seal member protrudes outward from the rear end of the tubular metallic member is 0.6 mm or more, the elastic seal member before compressive deformation needs be configured so that the axial length of the outer circumferential surface of the smaller diameter portion is 0.6 mm or more. Then, at the disposition step, it will suffice that the elastic seal member is disposed inside the tubular metallic member so that the axial distance between the rear end of the tubular metallic member and the rear end peripheral edge of the smaller diameter portion is 0.6 mm or more and then the process proceeds to the crimping step or the rate of deformation of the tubular metallic member at the crimping step is suitably adjusted so that the axial distance between the rear end of the tubular metallic member and the rear end peripheral edge of the smaller diameter portion becomes 0.6 mm or more for the first time when the elastic seal member is compressively deformed.

Further, in the above-described method for producing a gas sensor, it is preferably that the smaller diameter portion of the elastic seal member before compressive deformation has a nearly cylindrical section and a connecting section (stepped section) connecting between the cylindrical section and the main body portion and increasing in outer diameter gradually toward the main body portion.

In the method of producing a gas sensor is used the elastic seal member including the smaller diameter portion having, in a state before compressive deformation, the cylindrical section and the connecting section connecting between the cylindrical section and the main body portion and increasing gradually in outer diameter toward the main body portion. By forming the smaller diameter portion of the elastic seal member in such a manner, the outer circumferential surface of the smaller diameter portion can be easily disposed astride the rear end of the tubular metallic member when observed with respect to the axial direction of the gas sensor. In the meantime, by disposing the outer circumferential surface of the cylindrical section of the smaller diameter portion astride the rear end of the tubular metallic member, the stress caused by an edge or burr existing at the rear end portion of the tubular metallic member can be reduced effectively even when thermal deformation of the elastic seal member is caused.

Further, in the above-described method of producing a gas sensor, it is preferably that the outer circumferential surface of the smaller diameter portion of the elastic seal member before compressive deformation forms an inclined surface that tapers toward a rear end side.

In the method of producing a gas sensor according to the present invention is used the elastic seal member including the smaller diameter portion the outer circumferential surface of which forms an inclined surface that tapers toward the rear end side. Also in case the smaller diameter portion of the elastic seal member is so formed, the outer circumferential surface of the smaller diameter portion of the elastic seal member can be easily disposed astride the rear end of the tubular metallic member when observed with respect to the axial direction of the gas sensor.

Further, in the above-described method of producing a gas sensor, it is preferably that the relation of $0.7 \leq d/D < 1.0$ is satisfied where D is the inner diameter (unit: mm) of the rear end of the tubular metallic member and d is the outer diameter (unit: mm) of the smaller diameter portion of the elastic seal member corresponding in position to the rear end of the tubular metallic member after the disposition step.

By performing the crimping step after the disposition step so as to satisfy the above-described relationship of d/D, it becomes possible to produce a gas sensor which can attain a large freedom in the bending angle of the lead wire at the time of connection of the lead wire with an external circuit and can more assuredly prevent a crack in the elastic seal member, which is caused by thermal expansion of the elastic seal member.

If d/D is less than 0.7, there may occur such a case in which the lead wire contacts an edge or burr of the tubular metallic member when the bending angle of the lead wire is made large (e.g., nearly 180 degrees), even if a part of the smaller diameter portion is protruded from the rear end of the tubular metallic member after the crimping step, thus making it impossible to attain an effect of preventing damage of the lead wire sufficiently. On the other hand, if d/D is 1.0 or more, the outer circumferential surface of the smaller diameter portion, when thermally deformed, is liable to contact an edge or burr of the tubular metallic member and therefore there may possibly occur such a case in which the effect of preventing occurrence of a crack in the elastic seal member can not be obtained sufficiently even if the smaller diameter portion is provided to the elastic seal member.

Further, according to another aspect of the present invention, there is provided a method of producing a gas sensor having a sensor element extending in an axial direction and having a front end side to face a measured gas, a metallic housing radially surrounding the sensor element and holding the sensor element, a tubular metallic member provided to a rear end side of the metallic housing, at least one lead wire extending from an inside to an outside of the tubular metallic member and having a conductor wire electrically connected to the sensor element and an insulating film covering the conductor wire, and an elastic seal member having a lead wire insertion hole into which the lead wire is inserted, characterized by comprising a disposition step of disposing the elastic seal member inside the tubular metallic member so that the a portion of the elastic seal member protrudes outward from a rear end of the tubular metallic member, and a crimping step of crimping at least a portion of the tubular metallic member radially inward and thereby compressively deforming the elastic seal member, wherein the crimping step is performed under a condition where a space between the rear end of the tubular metallic member and an outer circumferential surface of the elastic seal member corresponding in position to the rear end of the tubular metallic member is larger than a space between an inner circumferential surface of a portion to be crimped of the tubular metallic member and an outer circumferential surface of the elastic seal member corresponding in position to the portion to be crimped of the tubular metallic member.

In the method of producing a gas sensor according to the present invention, the disposition step of disposing the elastic seal member within the tubular metallic member and the crimping step of crimping a portion of the tubular metallic member radially inward and fixing the elastic seal member to the tubular metallic member are performed in sequence.

In this connection, the crimping step is performed under the condition where the space between the rear end of the tubular metallic member and the outer circumferential surface of the elastic seal member is larger than the space between the inner circumferential surface of the portion to be crimped of the tubular metallic member and the outer circumferential surface of the elastic seal member. By performing the crimping step under such a condition, the rear end of the tubular metallic member and the outer circumferential surface of the elastic seal member can be easily put out of contact with each other after the crimped portion is formed (after the crimping step). The space between the rear end of the tubular metallic member and the outer circumferential surface of the elastic seal member is preferably in the range from about 0.2 to about 2.0 mm in consideration of deformation of the elastic seal member during the crimping step.

In the meantime, as a concrete method of making the space between the rear end of the tubular metallic member and the outer circumferential surface of the elastic seal member be larger than the space between inner circumferential surface of the portion to be crimped of the tubular metallic member and the outer circumferential surface of the elastic seal member can be enumerated the following methods. Namely, (1) a method of preparing beforehand an elastic seal member having a main body portion and a smaller diameter portion smaller in outer diameter than the main body portion, at a rear end side of the main body portion and disposing, in a disposition step, the entire main body portion and a part of the smaller diameter portion within the tubular metallic member while allowing a remaining part of the smaller diameter portion to protrude from the tubular metallic member, (2) a method of making the inner diameter at the rear end of the tubular metallic member be larger than the inner diameter of the portion to be crimped before the crimping step, and a method attained by a combination of the above-described methods (1) and (2).

By the gas sensor obtained in this manner by the method of the present invention, a portion of the elastic seal member protrudes from the rear end of the tubular metallic member, so that the lead wire, even when bent leftward or rightward at the time of connection to an external device, is hard to directly contact an edge or burr of the tubular metallic member and therefore damage of the lead wire can be prevented.

Further, by the gas sensor obtained by the method of the present invention, the crimping step is performed under the condition where a larger space is provided between the rear end of the tubular metallic member and the elastic seal member, so that it is easy to allow a space to remain between the rear end of the tubular metallic member and the elastic seal member after the crimping step. As a result, even when the elastic seal member is thermally expanded during use of the gas sensor, the elastic seal member is hard to contact the rear end of the tubular metallic member, thus making it possible to effectively reduce stress caused by contact with an edge or burr existing at the rear end of the tubular metallic member. In order to obtain such an effect sufficiently, it is preferable that a sufficient space (preferably in the range from 0.2 to 2.0 mm) is provided beforehand between the rear end of the tubular metallic member and the elastic seal member so that a space (preferably in the range from 0.1 to 1.5 mm) remains between the rear end of the tubular metallic member and the elastic seal member after the crimping step.

However, the above-described production method of the present invention is not limited to such one whereby a space remains between the rear end of the tubular metallic member and the elastic seal member after the crimping step but includes such one whereby the space is eliminated after the crimping step. In such a method, since a larger space has been provided between the rear end of the tubular metallic member and the elastic seal member than between the portion to be crimped and the elastic seal member, the contact pressure between the rear end of the tubular metallic member and the elastic seal member after the crimping step can be small and therefore damage of the elastic seal member can be reduced.

Thus, by the method of producing a gas sensor according to the present invention, it becomes possible to produce a highly reliable gas sensor which can prevent damage of the lead wire, which is caused by bending of the lead wire and prevent a crack of the elastic seal member even when the elastic seal member is thermally expanded during use of the gas sensor.

Further, a gas sensor according to a further aspect of the present invention comprises a sensor element extending in an axial direction and having a front end side to face a measured gas, a metallic housing radially surrounding the sensor element and holding the sensor element, a tubular metallic member provided to a rear end side of the metallic housing, at least one lead wire extending from an inside to an outside of the tubular metallic member and having a conductor wire electrically connected to the sensor element and an insulating film covering the conductor wire, and an elastic seal member having a lead wire insertion hole into which the lead wire is inserted, and is characterized in that a space is provided between the rear end of the tubular metallic member and the outer circumferential surface of the elastic seal member.

By the gas sensor of the present invention, a portion of the elastic seal member is protruded outward from the rear end of the tubular metallic member and an annular space is provided between the rear end (rear end of inner circumferential surface) of the tubular metallic member and the outer circumferential surface of the elastic seal member. By this, a portion of the elastic seal member is protruded from the rear end of the tubular metallic member, so that the lead wire is hard to directly contact an edge or burr of the tubular metallic member even when the lead wire is bent leftward or rightward at the time of connection to an external device, and therefore the gas sensor of the present invention can prevent damage of the lead wire.

Further, the gas sensor of the present invention is configured so that a space is provided between the rear end of the tubular metallic member and the elastic seal member at least at room temperature. Namely, since the rear end of the tubular metallic member is out of contact with the elastic seal member, non-contact of the rear end of the tubular metallic member and the elastic seal member can be maintained even when the elastic seal member is thermally expanded in use or the contact pressure can be small even when they are brought into contact with each other, thus making it possible to prevent damage of the elastic seal member.

Accordingly, the gas sensor of the present invention can be highly reliable and can prevent damage of the lead wire, which is caused by bending of the lead wire and prevent a crack of the elastic seal member even when the elastic seal member is thermally expanded during use of the gas sensor. In the meantime, in consideration of thermal expansion of the elastic seal member in use, the space between the rear end of the tubular metallic member and the elastic seal member at room temperature is preferably in the range from 0.1 to 1.5 mm.

Further, in the above-described gas sensor, it is preferable that the elastic seal member includes a main body portion disposed inside the tubular metallic member and a smaller diameter portion disposed at the more rear end side than the main body portion and smaller in outer diameter than the main body portion, and the space is provided between the rear end of the tubular metallic member and the smaller diameter portion.

By constructing in this manner so that the elastic seal member includes the main body portion and the smaller diameter portion smaller in outer diameter than the main body portion and disposing the main body portion inside the tubular metallic member while disposing the smaller diameter portion astride the rear end of the tubular metallic member, it becomes possible to form a space between the elastic seal member and the rear end of the tubular metallic member with ease and assuredness.

Further, in the above-described gas sensor, it is preferable that the tubular metallic member includes a fixing portion that fixes the elastic seal member to an inside thereof and a larger diameter portion disposed at the more rear end side than the fixing portion and larger in inner diameter than the fixing portion, and a space is formed between the larger diameter portion and the elastic seal member.

By providing, in this manner, the tubular metallic member with the fixing portion that fixes the elastic seal member inside thereof and the larger diameter portion larger in inner diameter than the fixing portion, it becomes possible to form a space between the elastic seal member and the tubular metallic member with ease and assuredness.

Further, in the above-described gas sensor, it is preferable that the elastic seal member protrudes outward from the rear end of the tubular metallic member along the axial direction by 0.6 mm or more.

By the gas sensor of the present invention, the length by which the elastic seal member protrudes outward from the rear end of the tubular metallic member is retained so as to be 0.6 mm or more. Due to this, even in the case where the lead wire is bent nearly 180 degrees at a point adjacent the rear end opening edge portion of the lead wire insertion hole of the elastic seal member at the time of connection to an external device, it is easy for the protruded portion of the elastic seal member to be interposed between the lead wire and an edge or burr of the tubular metallic member, thus making it possible to prevent damage of the lead wire more effectively.

BRIEF DESCRIPTION OF THE DRAWINGS

FIG. 3 is a view for explanation of an elastic seal member fixed to the outer tubular member of the gas sensor and in a state before compressive deformation.

DETAILED DESCRIPTION OF THE INVENTION

Figure 1:
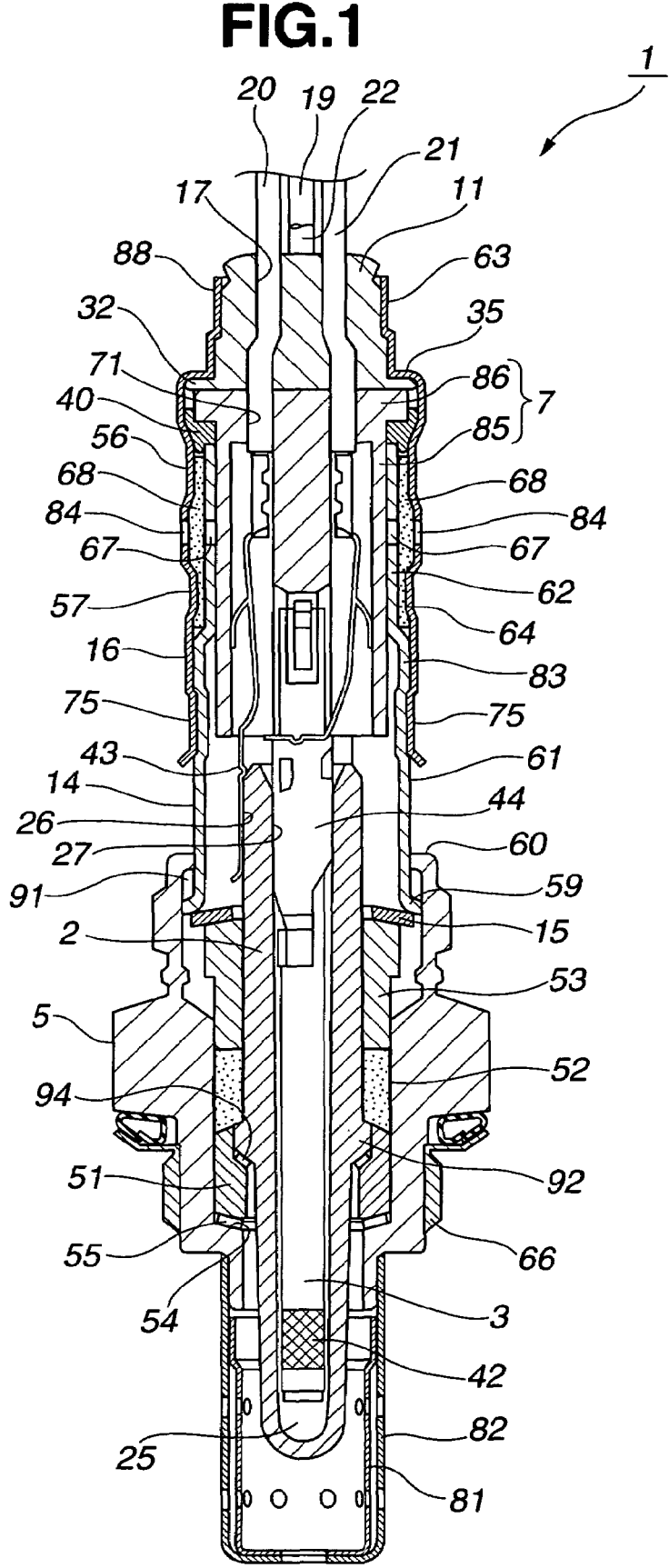
FIG. 1 is a sectional view showing an entire structure of a gas sensor according to an embodiment.

Hereinafter, a gas sensor embodying the present invention will be described with reference to the drawings. In this embodiment, description will be made as to a gas sensor (oxygen sensor) installed on an exhaust pipe of an automotive vehicle for detecting a concentration of oxygen contained in an exhaust gas. FIG. 1 is a sectional view for explanation of an entire structure of a gas sensor 1 according to this embodiment.

As shown in FIG. 1, the gas sensor 1 includes a sensor element having a bottomed tubular shape with a closed front end portion, containing, as a major component, partially stabilized zirconia including a solid solution of yttria as a stabilizer and having an oxygen ion conductivity, a ceramic heater 3 inserted into a bottomed hole 25 of the sensor element 2, and a metallic housing 5 supporting the sensor element 2 therewithin. In the meantime, in this embodiment, description is made by referring, of the directions along the axis of the sensor element 2 shown in FIG. 1, the side (closed side or lower side in the figure) directed toward a front end portion to be exposed to a measured gas (exhaust gas) as a "front end side" and the opposite side (upper side in the figure) as a "rear end side".

On an inner surface of the bottomed hole 25 of the sensor element 2 is formed in a way as to cover the inner surface nearly entirely an inner electrode layer 27 made of a Pt or Pt alloy so as to have a porous structure. On the other hand, on the outer surface of the sensor element 2 is formed a similar porous outer electrode layer 26. Further, at an axially nearly middle position of the sensor element 2 is provided an engagement flange 92 protruding radially outward. Further, the ceramic heater 3 is formed into a rod-like shape and has a heating portion 42 having inside thereof a heating resistor. The ceramic heater 3 generates heat when energized by way of heater lead wires 19 and 22, which will be described later and fulfils the function of heating the sensor element 2 for activating the sensor element 2.

The metallic housing 5 has a thread portion 66 for attaching the gas sensor 1 to an attached portion of an exhaust pipe and a hexagonal portion 93 to be engaged by an attaching tool at the time of attachment to the attached portion of the exhaust pipe. Further, the metallic housing 5 is configured so as to be able to accommodate therewithin a support member 51 made of alumina and supporting the front end side of the sensor element 2, a filling member 52 formed from talc powder and filled at the rear end side of the support member 51, and a sleeve 53 made of alumina and urging the filling member 52 from the rear end side to the front end side.

The metallic housing has at a front end side inner circumferential periphery a metallic housing side stepped portion 54 protruding radially inward, and the support member 51 is engaged with the metallic housing side stepped portion 54 by way of a packing 55. In the meantime, the sensor element 2 is supported by the metallic housing 5 by supporting the engagement flange portion 92 on the support member 51 by way of the packing 94. Between an inner surface of the metallic housing, which inner surface is position at the rear end side of the support member 51, and the outer surface of the sensor element 2 is disposed the filling member 52, and further at the rear end side of the filling member 52 are disposed in sequence and coaxially the sleeve 53 and an annular ring 15.

Further, into the inside at the rear end side of the metallic housing 5 is inserted a front end side of an inner tubular member 14 made of SUS304L. The inner tubular member 14 is fixed to the metallic housing 5 by crimping, under the condition where an increased diameter open end portion (front end opening end portion 59) at the front end side of the inner tubular member is abuttingly engaged with the annular ring 15, a metallic housing side rear end portion 60 inward and toward the front end. In the meantime, the gas sensor 1 is configured so that the filling member 52 is compressed and filled by way of the sleeve 53 when the metallic housing side rear end portion 60 of the metallic housing 5 is crimped, whereby the sensor element 2 is retained inside the tubular metallic housing 5 in an airtight manner.

The inner tubular member 14 is formed with an inner tube stepped portion 83 at an axially nearly middle position, an inner tube front end side body portion 61 at the front end side of the inner tube stepped portion 83 and an inner tube rear end side body portion 62 at the rear end side of the inner tube stepped portion 83. The inner tube stepped portion 62 is formed smaller in both inner and outer diameters than the inner tube front end side body portion 61 and formed so that its inner diameter is a little larger than the outer diameter of a separator main body portion 85 of a separator 7 which will be de described later. Further, the inner tube rear end side body portion 62 is formed with a plurality of air introducing holes 67 with predetermined circumferential intervals.

The outer tubular member 16 is formed into a tubular shape by deep drawing of a sheet material of SUS304L and formed with an outer tubular rear end side portion 63 having an opening for communication from the outside to the inside, at the rear end side, an outer tube front end side portion 64 coaxially connected to the inner tubular member 14 from the rear end side thereof, at the front end side and an outer tube stepped portion 53 connecting between the outer tube rear end side portion 63 and the outer tube front end side portion 64. In the meantime, the outer tube rear end side portion 63 is formed with a crimped portion 88 for fixing thereto the elastic seal member 11 in an airtight manner.

Further, to the front end side outer circumferential periphery of the metallic housing 5 is attached by welding a metallic, double-walled protector 81 that covers the front end portion of the sensor element 2 protruding from the front end of the metallic housing 5 and is formed with a plurality of gas inlet holes.

Figure 2:
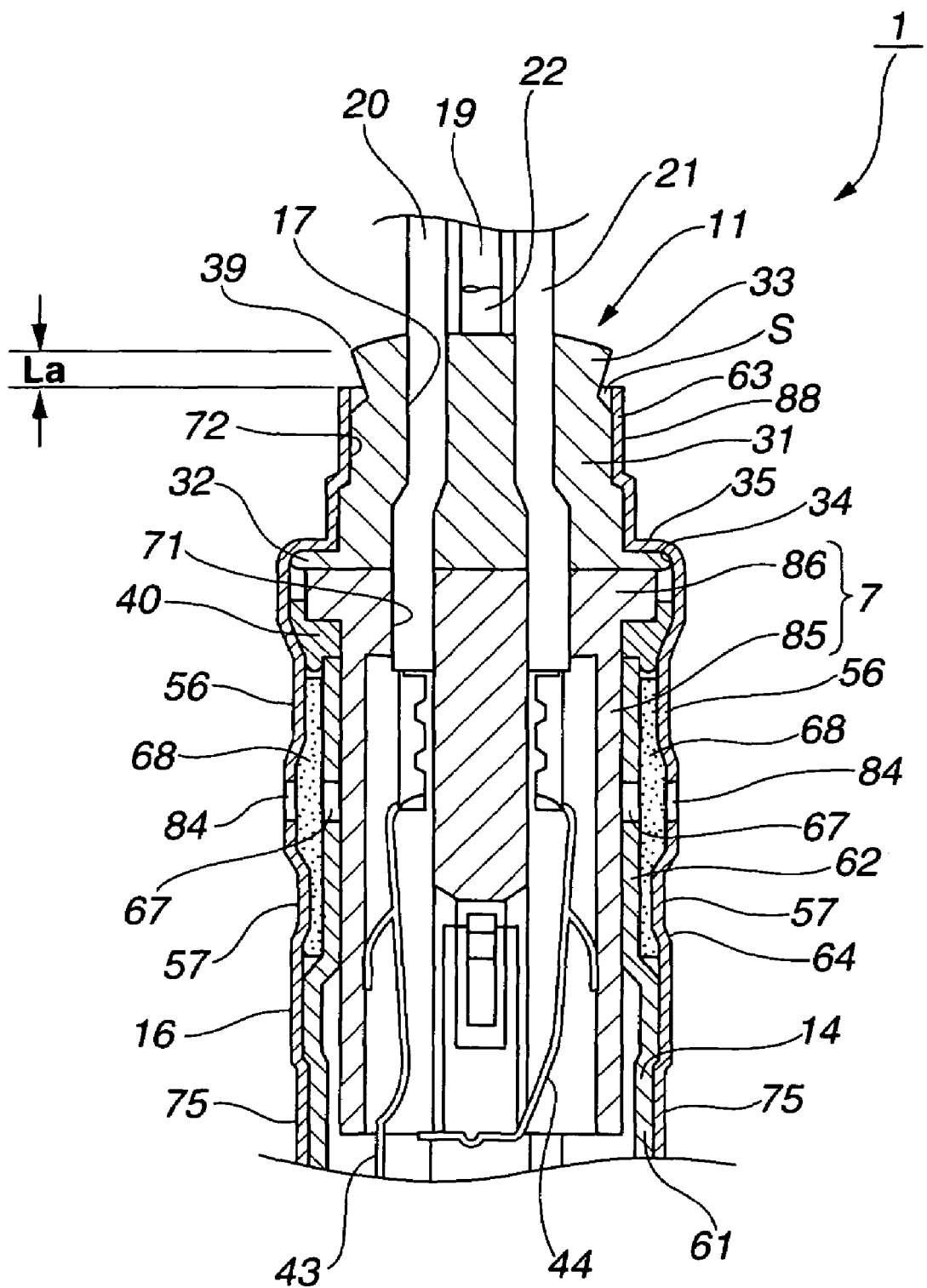
FIG. 2 is an enlarged sectional view of a connection portion of an outer tubular member and an inner tubular member of the gas sensor.

Then, an enlarged sectional view of the portion of the gas sensor 1, connecting between the outer tubular member 16 and the inner tubular member 14 is shown in FIG. 2

As shown in FIG. 2, outside the inner tube rear end side body portion 62 of the inner tubular member 14 is disposed a tubular filter 68 for preventing intrusion of water through the air introducing holes 67. In the meantime, the filter 68 is formed from a water-repellent filter such as a porous fabric of polytetrafuluoroethylene (trade name: Gore-Tex (Japan Gore-Tex Inc.)), which prevent passage of liquid containing water as a major constituent but allows passage of gas such as air.

The outer tube front end side portion 64 of the outer tubular member 16 is shaped so as to cover the inner tubular member 14 (specifically, the inner tubular rear end side body portion 62) in which the filter 68 is disposed, from the outside, and the outer tube front end side portion 64 is formed with a plurality of air introducing holes 84 along the circumferential direction and with predetermined intervals.

In the meantime, the outer tubular member 16 and the inner tubular member 14 are fixed to each other by a first crimped portion 56 which is formed by crimping at least a portion of the outer tube front end side portion 64 of the outer tubular member 16, which is positioned at the more rear end side than the air introducing holes 84, radially inward while interposing the filter 68 between the inner and outer tubular members and by a second crimped portion 57 which is formed by crimping at least a portion of the outer tube front end side portion, which is positioned at the more front end side than the air introducing holes 84 while similarly interposing the filter 68. In this instance, the filter 68 is held between the outer tubular member 16 and the inner tubular member 14 in an airtight manner. Further, the outer tube front end side portion 64 of the outer tubular member 16 is disposed so as to lie over the inner tube front end side body portion 61, and by crimping an at least part of an overlaid portion radially inward is formed a crimped connection portion 75.

By this, the open air that serves as a standard gas is introduced into the bottomed hole 25 of the sensor element 2 through the air introducing holes 84, the filter 68, the air introducing holes 67 and the inner tubular member 14. On the other hand, since a drop of water cannot pass the filter 68, its intrusion into the inner tubular member 14 is prevented.

The elastic seal member 11 disposed at the rear end and inside of the outer tubular member 16 (outer tube rear end side portion 63) is formed with four lead wire insertion holes 17 that extend through the elastic seal member from the front end side to the rear end side for inserting thereinto two element lead wires 20 and 21 for electrical connection with the sensor element 2 and two heater lead wires 19 and 22 for electrical connection with the ceramic heater 3.

Further, the separator 7 the front end side of which is inserted into the inner tube rear end side body portion 62 of the inner tubular member 14 is formed with separator lead wire insertion holes 71 that extend through the separator from the front end side to the rear end side for inserting thereinto the element lead wires 20, 21 and the heater lead wires 19, 22. Further, the separator 7 is formed with a bottomed retaining hole (no numeral) that extends in the axial direction and opens to the front end surface thereof. Into the retaining hole is inserted the rear end portion of the ceramic heater 3, and the rear end surface of the ceramic heater 3 is abuttingly engaged with the bottom surface of the retaining hole, whereby the ceramic heater 3 is axially positioned relative to the separator 7.

The separator 7 has a separator main body portion 85 inserted into the rear end side of the inner tubular member 14 and a separator flange 86 extending radially outward from the rear end portion of the separator main body portion 85. Namely, the separator 7 is disposed inside the outer tubular member 16 so as to be in a condition where the separator main body portion 85 is inserted into the inner tubular member 14 and the separator flange portion 86 is supported on the rear end surface of the inner tubular member 14 by interposing therebetween an annular seal member 40 made of fluororubber.

Further, the element lead wires 20, 21 and the heater lead wires 19, 22 are extended from the inside of the inner tubular member 14 and the outer tubular member 16 to the outside through the separator lead wire insertion holes 71 of the separator 7 and the lead wire insertion holes 17 of the elastic seal member 11. In the meantime, these four lead wires 19, 20, 21 and 22 are connected at the outside to a connector that is not shown. An external device such as ECU and the lead wires 19, 20, 21 and 22 perform input and output of electrical signals through the connector.

Further, each lead wire 19, 20, 21 or 22, though not shown in detail, has such a structure as to cover a conductor wire by an insulating film made of resin, and the rear end side of the conductor wire is connected to a connector terminal provided to the connector. The front end side of the conductor wire is connected by crimping to the rear end portion of a metallic terminal part 43 which is fitted on an outer surface of the sensor element 2, and the front end side of the conductor wire of the element lead wire 21 is connected by crimping to the rear end portion of a metallic terminal part 44 which is brought into contact with the inner surface of the sensor element 2 by press fitting. By this, the element lead wire 20 is electrically connected to the outer electrode layer 26 of the sensor element 2, and the element lead wire 21 is electrically connected to the inner electrode layer 27. On the other hand, the front end portions of the conductor wires of the heater lead wires 19 and 22 are connected to a pair of heater metallic terminal parts connected to heating resistors of the ceramic heater 3, respectively.

Then, the elastic seal member 11 that is a principal portion of the present invention will be described in detail.

The elastic seal member 11 is made of fluororubber that is excellent in heat resistance. In FIG. 3, the elastic seal member 11 in a state before compressive deformation (before being disposed in the outer tubular member 16) is shown. In the meantime, in FIG. 3, (a) is a perspective view of the elastic seal member 11, (b) is a plan view of the elastic seal member 11, which is obtained when the figure (a) is observed from the rear end side, and (c) is a side view of the elastic seal member 11, with a sectional representation taken along the line A-A in the figure (b).

As shown in FIG. 3, the elastic seal member 11 includes a main body portion 31, a seal member flange portion 32 extending radially outward from an outer circumferential surface 72 at the front end side of the main body portion 31 and a smaller diameter portion 33 smaller in outer diameter than the main body portion 31. There are formed four lead wire through holes 17 in a way as to penetrate the main body portion 31 and the smaller diameter portion 33 axially. In the meantime, the length (height) Xe along the axial direction of the elastic seal member 11 before compressive deformation is 7.0 mm in this embodiment.

The main body portion 31 is cylindrical and 8.6 mm in the outer diameter Xa. The seal member flange portion 32 is 12.4 mm in the outer diameter Xd and has a thick-walled section 34 larger in thickness than a connecting section connected to the main body portion 31. The thick-walled section 34 is shaped so that a circular cross section of the diameter Xf of 1.0 mm continues annularly.

Further, the smaller diameter portion 33 is configured to include a cylindrical section 38 and a connecting section 36 connecting between the cylindrical section 38 and the main body portion 31. The connecting section 36 is shaped so as to increase in outer diameter toward the main body portion 31 gradually and curvedly. The axial size (height) Xh of the smaller diameter portion 33 is 1 mm in this embodiment, and the outer diameter Xi at the rear end surface is 7.4 mm. Further, the curved surface of the connecting section 36 is 0.3 mm in the radius of curvature.

As shown in FIG. 2, by crimping a portion of the outer tubular member 16, which is positioned at the outer circumferential side of the seal member 11, radially inward and thereby forming a crimped portion 88, the elastic seal member 11 is fixed to the outer tubular member 16 while being in a compressively deformed state. In this instance, the elastic seal member 11 of the gas sensor 1 of this embodiment is fixed to the outer tubular member 16 in such a manner that the outer circumferential surface 72 of the main body portion 31 does not protrude outward from the rear end of the outer tubular member 16 but a part (only the rear end side) of the smaller diameter section 33 (specifically, the cylindrical section 38) protrudes from the rear end of the outer tubular member 16. In this manner, in the gas sensor 1 of this embodiment, the outer circumferential surface of the smaller diameter section 33 is disposed astride the rear end of the outer tubular member, and further an annular space S is formed between the outer circumferential surface of the smaller diameter section 33 and the rear end (rear end of the inner circumferential surface) of the outer tubular member 16. In the meantime, the axial distance (shortest distance) between the rear end of the outer tubular member 16 and the rear end surface peripheral edge 39 of the smaller diameter section 33 of the elastic seal member 11 is 1.2 mm in this embodiment.

Further, as shown in FIG. 2, the seal member flange portion 32 of the elastic seal member 11 is disposed so as to be interposed between the outer tubular member 16 (specifically, the inner surface of the outer tube stepped portion 35) and the separator 7. The thick-walled section 34 of the seal member flange portion 32 is formed so that the circular cross section continues annularly as described above and is varied in cross sectional shape when interposed between the outer tube stepped portion 35 and the separator flange portion 86, whereby to prevent a space from being caused between the inner surface of the outer tubular member 16 and the separator and thereby improve the airtightness and the waterproof between the outer tubular member 16 and the separator 7.

The gas sensor 1 is produced in the following manner.

In advance, the element lead wires 20 and 21 are connected to the respective metallic terminal parts 43 and 44 beforehand, and the heater lead wires 19 and 22 are connected to the heater metallic terminal parts of the ceramic heater 3. Then, under the condition where the ceramic heater 3 is positioned inside the metallic terminal part 44, the lead wires 19, 20, 21 and 22 are inserted into the respective separator lead wire insertion holes 71 of the separator 7. Then, under the condition where the lead wires 19, 20, 21 and 22 are inserted into the lead wire insertion holes 17 of the elastic seal member 11, the elastic seal member 11 is moved until the front end surface thereof is abuttingly engaged with the rear end surface of the separator 7. In this manner, a sensor upper portion intermediate assembly (refer to FIG. 5) is produced. In the meantime, as the elastic seal member 11 is used such one that is formed into the shape shown in FIG. 3 by injection molding or the like. Further, to the outer circumferential periphery of the separator main body portion 85 is attached beforehand an annular seal member 40.

Figure 4:
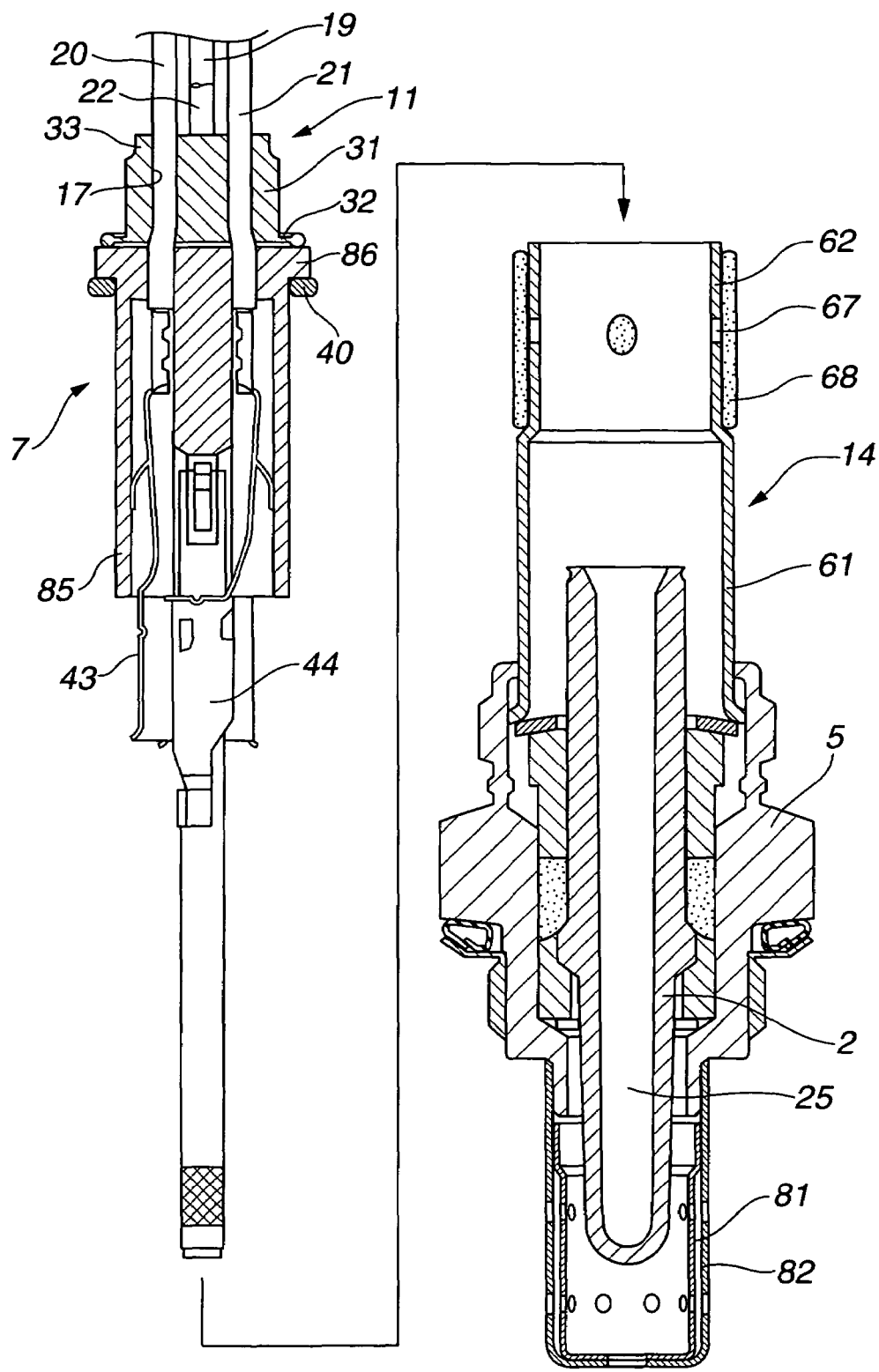
FIG. 4 is a view for explanation of how a ceramic heater of a sensor upper intermediate assembly is introduced and inserted into a bottomed hole of a sensor element of a sensor lower intermediate assembly.

Then, as shown in FIG. 4, a sensor lower portion intermediate assembly is prepared in which the sensor element 2 is held by the metallic housing 5, the protectors 81 and 82 are welded to the front end side of the metallic housing 5 and the front end side of the inner tubular member 14 is connected to the rear end side of the metallic housing. In the meantime, around the inner tube rear end body portion 62 of the inner tubular member 14 is disposed a tubular filter 68. Then, the separator main body portion 85 of the separator 7 of the sensor upper portion intermediate assembly is positioned inside the inner tube rear end body portion 62 of the inner tubular member 14 of the sensor lower portion intermediate assembly. By this, the metallic terminal part 43 is inserted into the bottomed hole 25 of the sensor element 2 together with the ceramic heater 3 and is electrically connected to the outer electrode layer 26.

Then, the outer tubular member 16 is disposed so as to lie over the outside of the inner tube front end side body portion 62 of the inner tubular member 14. Then, the overlaid portions of the outer tubular member 16 and the inner tube front end side body portion 62 is driven radially inward by crimping while pushing the outer tube stepped portion 35 axially toward the front end side, whereby a crimped connection portion 75 is formed to fix the outer tubular member 16 and the inner tubular member 14 to each other. In the meantime, the crimping is performed by eight-directional round crimping.

Figure 5:
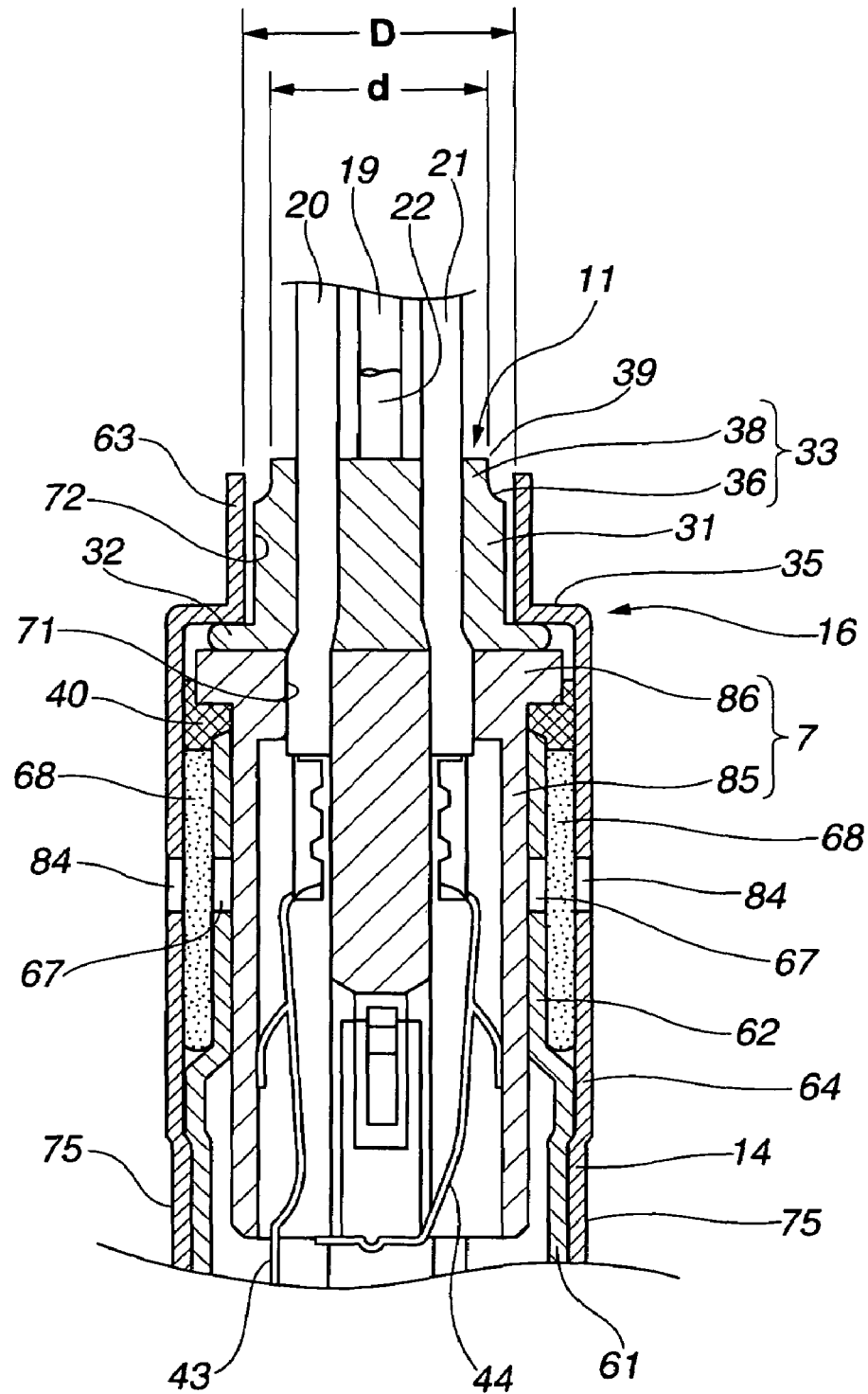
FIG. 5 is a view for explanation of a disposition step of disposing an elastic seal member before compressive deformation inside a rear end portion of the outer tubular member.

Herein, as shown in FIG. 5, the elastic seal member 11 immediately after the crimped connection portion 75 is formed is in a state wherein the entire main body portion 31 and the front end side of the smaller diameter section are disposed inside the outer tubular member 16 and the outer circumferential surface of the cylindrical section 38 is disposed astride the rear end of the outer tubular member 16 when observed with respect to the axial direction. Namely, in this embodiment, the dimensions of the various portions of the elastic seal member 11 and the outer tubular member 16 are adjusted so that when the elastic seal member 11 is disposed inside the outer tubular member 16, the entire main body portion 31 of the elastic seal member 11 is disposed inside the outer tubular member 16 and the rear end side of the cylindrical section 38 of the smaller diameter portion 33 protrudes outward from the rear end of the outer tubular member 16.

Further, in this embodiment, when the elastic seal member 11 is disposed inside the outer tubular member 16, the inner diameter D at the rear end of the outer tubular member 16 is 8.9 mm, the outer diameter d of the smaller diameter portion 33 (e.g., cylindrical section 38) is 7.4 mm, and the space between the rear end of the outer tubular member 16 and its corresponding smaller diameter portion 33 is 0.75 mm. In contrast to this, the space between a portion to be crimped of the outer tubular member 16 and its corresponding main body portion 31 is 0.15 mm. In this manner, the space between the rear end of the outer tubular member 16 and the elastic seal member 11 is larger than that between the portion to be crimped of the outer tubular member 16 and the elastic seal member 11. Further, the relation between the rear end inner diameter D and the outer diameter d is determined so that d/D=0.83.

Figure 6:
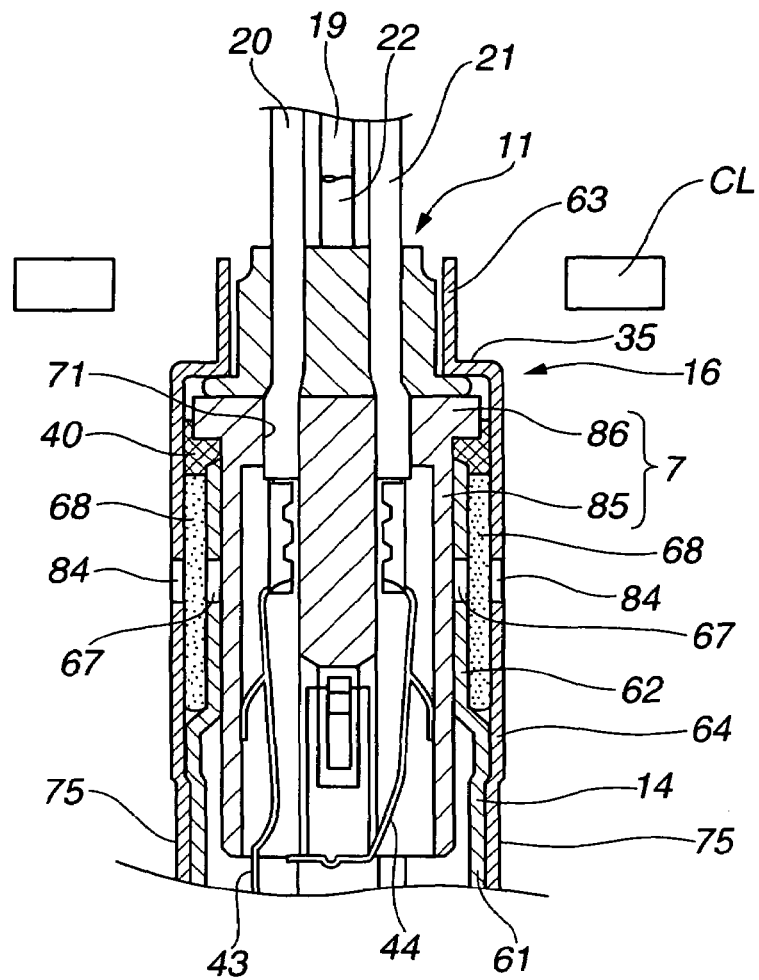
FIG. 6 is a view for explanation of a crimping step of crimping a portion of the outer tubular member, which is positioned outside an outer circumferential surface of a main body portion of the elastic seal member radially inward.

Then, as shown in FIG. 6, the portion of the outer tubular member 16 (outer tube rear end side portion 63), which is positioned outside the outer circumferential surface of the elastic seal member 11, is crimped radially inward by using crimping tools CL, thereby forming the crimped portion 88 and compressively deforming the elastic seal member 11. By this, the elastic seal member 11 is fixed to the outer tubular member 16 in an airtight manner. This crimping is also performed by eight-directional round crimping. In this instance, the deformation rate of the outer tubular member 16 by crimping is adjusted so that the outer circumferential surface 72 of the main body portion 31 is never protruded outward from the rear end of the outer tubular member 16. In the meantime, after the crimped portion 88 is formed, an axial distance La (refer to FIG. 2) between the rear end of the outer tubular member 16 and the rear end surface peripheral edge 39 of the smaller diameter portion 33 is 1.2 mm.

Then, the outer tubular member 16 and the inner tubular member 14 that are fixed by the crimped connection portion 75 are formed with a first crimped portion 56 and a second crimped portion 57, whereby to complete the gas sensor 1.

As having been described, the gas sensor 1 of this embodiment is formed by using the elastic seal member 11 that has the smaller diameter portion 33 positioned at the most rear side and the main body portion 31 positioned at the more front end side than the smaller diameter portion and larger in outer diameter than the smaller diameter portion 33. The elastic seal member 11 is disposed so that the entire main body portion 31 is disposed inside the outer tubular member 16 and the outer circumferential surface of the smaller diameter portion 33 (specifically, the outer circumferential surface of the cylindrical section 38) is disposed astride the rear end of the outer tubular member 16 when observed with respect to the axial direction of the gas sensor 1. Further, in the gas sensor 1 of this embodiment, the elastic seal member 11 protrudes outward from the rear end of the outer tubular member 16 and the space S (in the range from about 0.1 to about 0.5 mm in this embodiment) is formed between the outer circumferential surface of the elastic seal member 11 and the rear end of the outer tubular member 16.

By this, in the gas sensor 1, the lead wires 19, 20, 21 and 22, even when bent leftward and rightward at the time of connection to an external device by way of connectors, are hard to directly contact an edge or burr existing at the rear end of the outer tubular member 16 and therefore can be prevented from being damage. Particularly, in the gas sensor 1, the axial distance La of 1.2 mm is secured between the rear end of the outer tubular member 16 and the rear end surface peripheral edge of the elastic seal member 11, so that even when the lead wire is bent nearly 180 degrees at a point adjacent the rear end opening edge portion of the lead wire insertion hole of the elastic seal member, damage of the lead wire can be prevented effectively.

Further, even when the elastic seal member 11 is thermally expanded during use of the gas sensor 1 in a high temperature environment, occurrence of a crack in the elastic seal member 11 due to thermal expansion can be prevented since the a part of the smaller diameter portion 33 (specifically, the cylindrical section 38) that is formed smaller in diameter than the main body portion 31 is protruded from the rear end of the outer tubular member 16.

In the foregoing, the present invention has been described with respect to the embodiments, it is needless to say that the present invention is not limited to the embodiments described as above but various modifications and variations may be made thereto within the scope of the subject matter of the present invention.

Figure 7:
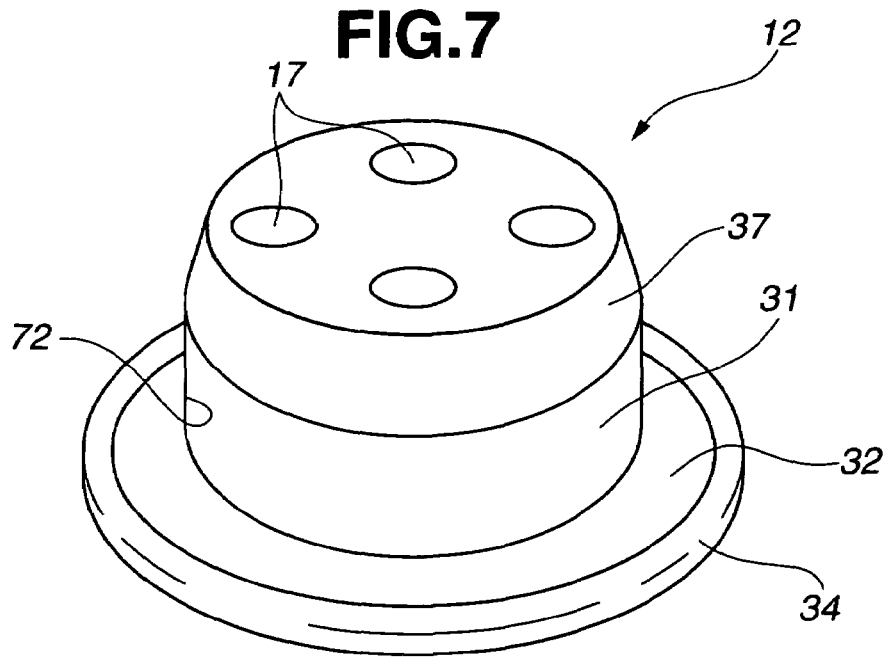
FIG. 7 is a perspective view of a second elastic seal member in a state before compressive deformation.

For example, while in the embodiments described as above, the elastic seal member 11 in which the smaller diameter portion at the rear end side of the main body portion 31 includes the connecting section 36 and the cylindrical section 38 is shown by way of example, the smaller diameter portion 33 suffices if shaped so as to be smaller in diameter than the main body portion 33. Specifically, as shown in FIG. 7, there can be used a second elastic seal member 12 that includes, similarly to the above-describe embodiment, a main body portion 31, a seal member flange portion 32 and a second smaller diameter portion 37 positioned at the rear end side of the main body portion 31 and having an outer circumferential surface that reduces in diameter toward the rear end side (tapered surface)

However, also in case the second seal member 12 is used, it is required, at the time of disposing the second elastic seal member 12 inside the outer tubular member 16, to dispose the second elastic seal member 12 in the outer tubular member 16 in such a manner that the entire main body portion 31 of the second elastic seal member 12 is disposed inside the outer tubular member 16 and the rear end side of the second smaller diameter portion 37 protrudes outward from the rear end of the outer tubular member 16. Further, at the time the second elastic seal member 12 is to be compressively deformed and fixed to the outer tubular member 16, it is required to crimp the outer tubular member 16 radially inward so that the outer circumferential surface 72 of the main body portion 31 does not protrude outward from the rear end.

Further, while in the above-described embodiment the smaller diameter portion 33 of the elastic seal member 11 is positioned at the most rear end side, the smaller diameter portion 33 is not necessarily positioned at that place.

Further, while in the above-described embodiment the gas sensor 1 has been described as an oxygen sensor, the present invention can be applied to another gas sensor such as NOx sensor and HC sensor.

Further, in the above-described embodiment, used as the sensor element 2 is such one that is closed at the front end. However, the sensor element may vary in shape according to the gas to be detected and a plate-shaped sensor element may be used.

Figure 8:
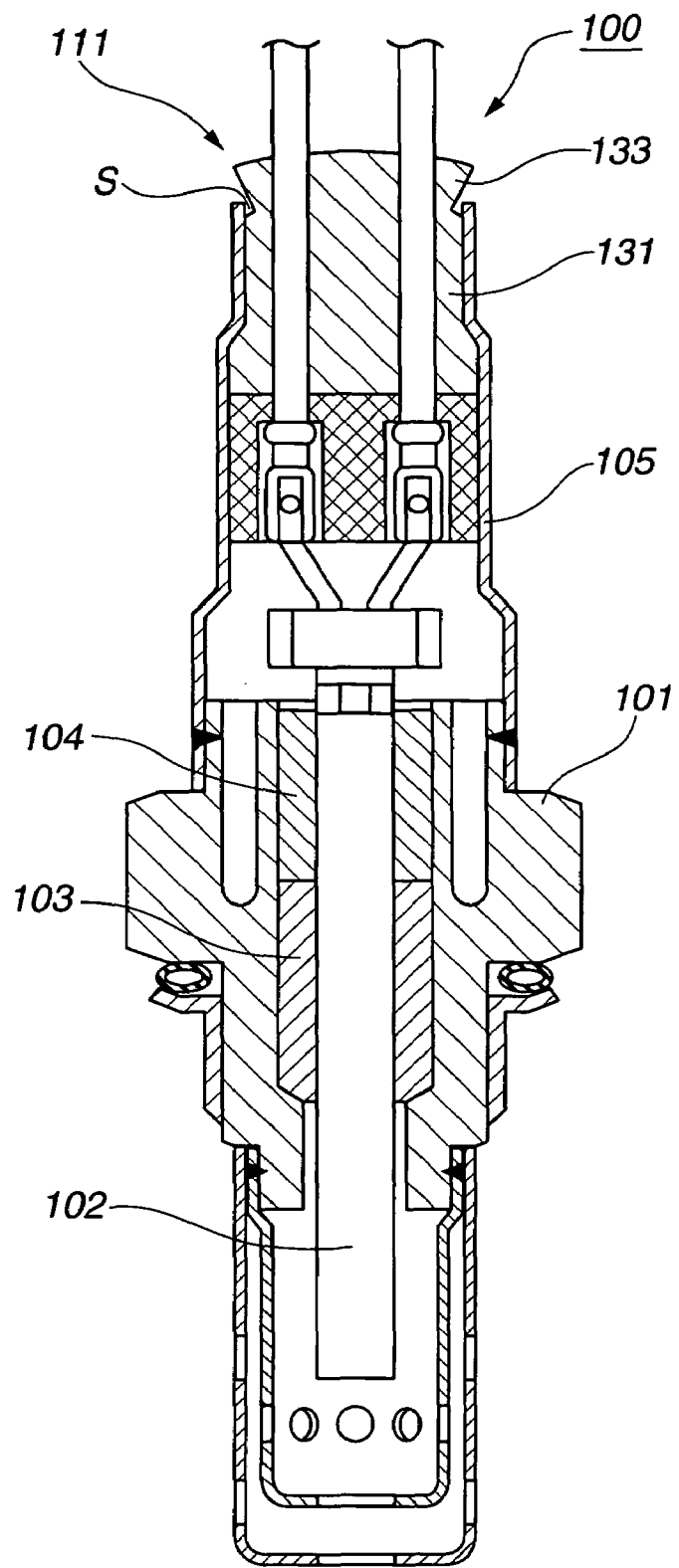
FIG. 8 is a sectional view showing an entire structure of a second gas sensor using a plate-shaped sensor element.

A second gas sensor 100 in which a plate-shaped sensor element is employed is shown in FIG. 8. In FIG. 8, a tubular metallic member is not dual-walled so as to include, as in the above-described embodiment, the outer tubular member 16 and the inner tubular member 14 but single-walled and constituted by an outer tubular member 105. The outer tubular member 105 is connected to the rear end outer periphery of the metallic housing 101 by all-round laser welding. In the meantime, the plate-shaped sensor element 102 is held inside the metallic housing 101 in an airtight manner by filling members 103 and 104 containing crystallized glass powder.

Also in the second gas sensor 100, a third elastic seal member 111 is fixed to the rear end side of the outer tubular member 105 while being in a compressively deformed state. More specifically, by crimping the rear end side of the outer tubular member 105 radially inward, the third elastic seal member 111 is fixed in an airtight manner. In the meantime, the third seal member 111 has the same shape as the elastic seal member 11 shown in the above-described embodiment except that the elastic seal member flange portion 12 is not provided.

Further, as shown in FIG. 8, the third elastic seal member 111 is fixed to the outer tubular member 105 in such a manner that the entire main body portion 131 is disposed inside the outer tubular member 105 and the rear end side of the third smaller diameter portion 133 protrudes outward from the rear end of the outer tubular member 105. Namely, the outer circumferential surface of the third smaller diameter portion 133 is disposed astride the rear end of the outer tubular member 105.

By this, the second gas sensor 100 also can attain the same operation and effect as the above-described embodiment.

Further, while in the above-described embodiment description has been made as to the structure in which the elastic seal member 11 is provided with the smaller diameter portion 33, and the smaller diameter portion 33 is made to protrude from the rear end of the outer tubular member 16 while forming the annular space S between the outer circumferential surface of the smaller diameter portion 33 and the rear end of the outer tubular member 16, the structure for forming the space between the outer circumferential surface of the elastic seal member 11 and the rear end of the outer tubular member 16 is not limited to that described as above.

Figure 9:
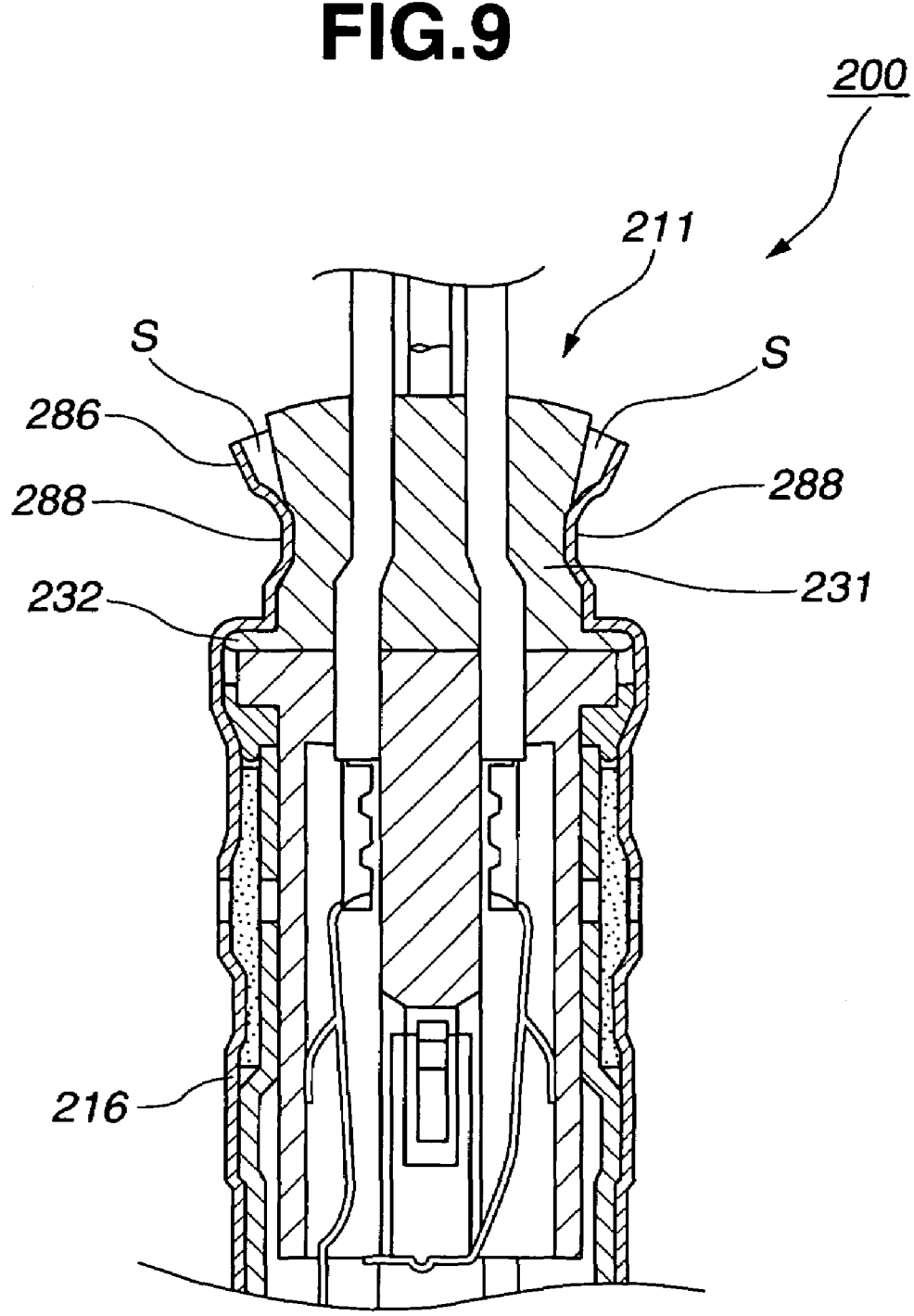
FIG. 9 is an enlarged sectional view of a principal portion of a third gas sensor in which an outer tubular member is formed with, beforehand, an larger diameter portion larger in inner diameter than a crimped portion at a more rear end side than the crimped portion.

Specifically, by additional reference to FIG. 3, a fourth elastic seal member that is not formed with the smaller diameter portion 33 but includes a main body portion and a seal member flange portion is prepared. As shown in FIG. 9, a third gas sensor 200 is formed so that part of a main body portion 231 and a seal member flange portion 232 of a fourth elastic seal member 211 are fixed within an outer tubular member 216 and the remaining part of the main body portion 231 protrudes outward from the rear end of the outer tubular member 216. In the meantime, since the third gas sensor 200 differs from the gas sensor 1 of the above-described embodiment in the shape of the elastic seal member and the structure at the rear end of the outer tubular member, the portions different from the gas sensor 1 will hereinafter be described concentratively and like portions thereto are omitted for brevity.

In the meantime, in the gas sensor 1 of the above-described embodiment, the outer tubular member 16 is formed, and the crimped portion 88 is formed after the elastic seal member 11 is disposed inside the outer tubular member 16. On the other hand, in the third gas sensor 200, at the more rear end side than a portion to be formed with a crimped portion 288 (hereinafter referred to as a portion to be crimped) is formed beforehand a larger diameter portion 286 larger in inner diameter than the portion to be crimped, so that the rear end inner diameter of the outer tubular member 216 is larger in inner diameter than the portion to be crimped. In the meantime, the dimensions of the various portions of the fourth elastic seal member 211 and the outer tubular member 216 are adjusted beforehand so that the inner diameter of the portion to be crimped and the inner diameter of the larger diameter portion 286 are larger than the outer diameter of the main body portion 231 of the fourth elastic seal member 211.

Then, the fourth elastic seal member 211 is disposed inside the outer tubular member 216, and under the condition where a part of the main body portion 232 is protruded outward from the rear end of the outer tubular member 216, the portion to be crimped, which is positioned outside the outer circumferential surface of the fourth elastic seal member 211, is crimped radially inward to form the crimped portion 288 while compressively deforming the fourth seal member 211. Since the larger diameter portion 286 larger in inner diameter than the portion to be crimped of the outer tubular member 216 has been formed beforehand, in spite of deformation of the fourth elastic seal member 211 at the crimping step, an annular space S between the outer circumferential surface of the fourth elastic seal member 211 and the rear end of the outer tubular member 216 is obtained even at the crimping step.

By this, also in the third gas sensor 200, a portion of the fourth elastic seal member 211 protrudes outward from the rear end of the outer tubular member 216 and the space S is formed between the outer circumferential surface of the fourth elastic seal member 211 and the rear end of the outer tubular member 216, so that the same operation and effect as in the above-described embodiments can be obtained.

TEST EXAMPLES

To confirm the effect of the present invention, the following test was carried out.

As an example 1 of the gas sensor was prepared such one in which the axial distance between the rear end surface peripheral edge 39 of the elastic seal member 11 and the rear end of the outer tubular member 16 as described in the above-described embodiment was 1.2 mm. As an example 2 of the gas sensor was prepared such one that was the same as the above-described example 1 except that the axial distance between the rear end surface peripheral edge 39 of the elastic seal member and the rear end of the outer tubular member 16 was 0.6 mm. Further, as an example 3 of the gas sensor was prepared such one in which the above-described second seal member 12 was used in place of the elastic seal member 11 in the above-described embodiment, the main body portion 31 was accommodated within the outer tubular member 16 and only a part of the smaller diameter portion 37 was protruded from the rear end of the outer tubular member 16. The axial distance between the rear end surface peripheral edge of the second elastic seal member 12 and the rear end of the outer tubular member 16 was 0.4 mm.

Further, as a comparative example 1 was prepared such one in which a conventional cylindrical elastic seal member that was not formed with a smaller diameter potion was used in place of the elastic seal member 11 in the above-described embodiment, and the rear end side of the main body portion does not protrude from the rear end of the outer tubular member at all. Further, as a comparative example 2 was prepared such one in which the same elastic seal member as the comparative example 1 was used and the rear end of the elastic seal member was protruded from the rear end of the outer tubular member. In the meantime, the comparative example 2 was prepared so as to be 0.6 mm in the axial distance between the rear end surface peripheral edge of the main body portion and the rear end of the outer tubular member. Ten sensors were prepared to each of the examples 1 to 3 and the comparative examples 1 and 2.

In those five kinds of gas sensors, four lead wires were first bent 180 degrees in the same direction at the points adjacent the rear end opening edge portions of the lead wire insertion holes, and under such a condition the lead wires were pulled with pulling forces of 80N and 100N. Thereafter, it was visually observed whether damage was caused in the insulating film of the lead wire. The number of examples in which damage of the insulating film of the lead wire was observed for ten gas sensors of each kind was shown in Table 1.

Then, each gas sensor was heat-treated so that the elastic seal member was held at 260° C. and this heat-treatment was continued for fifty hours. Thereafter, it was visually observed whether a crack was caused in the external appearance of the elastic seal. The number of examples, in which a crack was caused in the elastic seal member, for ten gas sensors of each kind was additionally described in Table 1.

In Table 1, in consideration of both of the result of the lead wire pulling test and the result of the elastic seal member heating test, the example the both results of which were very good was indicated by ○, the example the both results of which was good was indicated by Δ, and the example which effected other results was indicated by X, and an integrated evaluation was made.

TABLE 1

|  | The number of examples in which damage was caused by puling test | | The number of examples in which crack was caused in elastic seal member by heating test | Integrated evaluation |
| --- | --- | --- | --- | --- |
|  | 80 N | 100 N | | |
| Example 1 | 0/10 | 0/10 | 0/10 | ○ |
| Example 2 | 0/10 | 0/10 | 0/10 | ○ |
| Example 3 | 0/10 | 1/10 | 0/10 | Δ |
| Comparative Example 1 | 6/10 | 8/10 | 0/10 | X |
| Comparative Example 2 | 0/10 | 0/10 | 7/10 | X |

By the Table 1, it was confirmed that in case of the gas sensors according to the examples 1 to 3, there was not caused any damage in the lead wires even when the lead wires were pulled in the same direction with a pulling force of 80N and there was not caused any crack in the elastic seal member and therefore they could be good gas sensors. Particularly, in case of the gas sensors 1 according to the examples 1 and 2, in which the axial distance between the rear end peripheral surface of the elastic seal member and the rear end of the outer tubular member was 0.6 mm or more, damage of the lead wires was not observed at all even when the lead wires were pulled with a pulling force of 100N.

On the other hand, in case of the comparative example 1 in which the conventional elastic seal member which does not have a smaller diameter portion was used, though a crack in the elastic seal member was not observed, it was confirmed that the lead wires had a tendency to be liable to be damage. Further, in case of the comparative example 2 in which the same convention type elastic seal member was used, though damage of the lead wires were prevented by the effect of the distance between the rear end outer circumferential surface of the elastic seal member and the rear end of the outer tubular member being 0.6 mm, it was confirmed that the elastic seal member had a tendency to be liable to be damaged since differing from the examples 1 to 3, the portion of the elastic seal member, which was protruded outward from the rear end of the outer tubular member, was not formed smaller in diameter.

The invention claimed is:

1. A method of producing a gas sensor having a sensor element extending in an axial direction and having a front end side to face a measured gas, a metallic housing holding therein the sensor element, a tubular metallic member provided to a rear end side of the metallic housing, at least one lead wire extending from an inside to an outside of the tubular metallic member and having a conductor wire electrically connected to the sensor element and an insulating film covering the conductor wire, and an elastic seal member having a lead wire insertion hole into which the lead wire is inserted, the method comprising:

a disposition step of preparing the elastic seal member having a main body portion and a smaller diameter portion smaller in outer diameter than the main body portion, disposing the entire main body portion and a part of the smaller diameter portion inside the tubular metallic member and allowing a remaining part of the smaller diameter portion to protrude outward from a rear end of the tubular metallic member, wherein the at least one wore extends through the smaller diameter portion of the elastic seal member; and a crimping step of crimping at least a portion of the tubular metallic member radially inward and thereby compressively deforming the elastic seal member.

2. A method according to claim 1, wherein the elastic seal member protrudes outward from the rear end of the tubular metallic member along the axial direction by 0.6 mm or more after the crimping step.

3. A method according to claim 1, wherein the smaller diameter portion of the elastic seal member before compressive deformation has a nearly cylindrical section and a connecting section connecting between the cylindrical section and the main body portion and increasing in outer diameter gradually toward the main body portion.

4. A method according to claim 3, wherein the relation of $0.7 \leq d/D < 1.0$ is satisfied where D is the inner diameter (unit: mm) of the rear end of the tubular metallic member and d is the outer diameter (unit: mm) of the smaller diameter portion of the elastic seal member corresponding in position to the rear end of the tubular metallic member after the disposition step.

5. A method according to claim 1, wherein the outer circumferential surface of the smaller diameter portion of the elastic seal member before compressive deformation tapers toward a rear end side.

6. A method of producing a gas sensor having a sensor element extending in an axial direction and having a front end side to face a measured gas, a metallic housing holding therein the sensor element, a tubular metallic member provided to a rear end side of the metallic housing, at least one lead wire extending from an inside to an outside of the tubular metallic member and having a conductor wire electrically connected to the sensor element and an insulating film covering the conductor wire, and an elastic seal member having a lead wire insertion hole into which the lead wire is inserted, the method comprising:

a disposition step of disposing the elastic seal member inside the tubular metallic member so that the a portion of the elastic seal member protrudes outward from a rear end of the tubular metallic member; and a crimping step of crimping at least a portion of the tubular metallic member radially inward and thereby compressively deforming the elastic seal member;

wherein the crimping step is performed under a condition where a space between the rear end of the tubular metallic member and the outer circumferential surface of the elastic seal member corresponding in position to the rear end of the tubular metallic member is larger than a space between an inner circumferential surface of a portion to be crimped of the tubular metallic member and the outer circumferential surface of the elastic seal member corresponding in position to the portion to be crimped of the tubular metallic member.

7. A gas sensor comprising:

a sensor element extending in an axial direction and having a front end side to face a measured gas;

a metallic housing holding therein the sensor element;

a tubular metallic member provided to a rear end side of the metallic housing;

at least one lead wire extending from an inside to an outside of the tubular metallic member and having a conductor wire electrically connected to the sensor element and an insulating film covering the conductor wire; and an elastic seal member having a lead wire insertion hole into which the lead wire is inserted, wherein a space is provided between the rear end of the tubular metallic member and the outer circumferential surface of the elastic seal member, wherein the elastic seal member includes a main body portion disposed inside the tubular metallic member and a smaller diameter portion disposed at the more rear end side than the main body portion and smaller in outer diameter than the main body portion, and the space is provided between the rear end of the tubular metallic member and the smaller diameter portion, and wherein a portion of the elastic seal member protrudes outward from the rear end of the tubular metallic member.

8. A gas sensor comprising;

a sensor element extending in an axial direction and having a front end side to face a measured gas;

a metallic housing holding therein the sensor element;

a tubular metallic member provided to a rear end side of the metallic housing;

at least one lead wire extending from an inside to an outside of the tubular metallic member and having a conductor wire electrically connected to the sensor element and an insulating film covering the conductor wire; and an elastic seal member having a lead wire insertion hole into which the lead wire is inserted, wherein a space is provided between the rear end of the tubular metallic member and the outer circumferential surface of the elastic seal member, and wherein a portion of the elastic seal member protrudes outward from the rear end of the tubular metallic member; wherein the tubular metallic member includes a fixing portion that fixes the elastic seal member to an inside thereof and a larger diameter portion disposed at the more rear end side than the fixing portion and larger in inner diameter than the fixing portion, and the space is formed between the larger diameter portion and the elastic seal member.

9. comprising:

a sensor element extending in an axial direction and having a front end side to face a measured gas;

a metallic housing holding therein the sensor element;

a tubular metallic member provided to a rear end side of the metallic housing;

at least one lead wire extending from an inside to an outside of the tubular metallic member and having a conductor wire electrically connected to the sensor element and an insulating film covering the conductor wire; and an elastic seal member having a lead wire insertion hole into which the lead wire is inserted, wherein a space is provided between the rear end of the tubular metallic member and the outer circumferential surface of the elastic seal member, wherein a portion of the elastic seal member protrudes outward from the rear end of the tubular metallic member, and wherein the elastic seal member protrudes outward from the rear end of the tubular metallic member along the axial direction by 0.6 mm or more.

* * * * *